(12) United States Patent
Gilbride

(10) Patent No.: US 8,157,849 B1
(45) Date of Patent: Apr. 17, 2012

(54) TANNING BED WITH AN AIR FILTER

(76) Inventor: Brian Gilbride, Moscow, PA (US)

( * ) Notice: Subject to any disclaimer, the term of this patent is extended or adjusted under 35 U.S.C. 154(b) by 2130 days.

(21) Appl. No.: 10/737,886

(22) Filed: Dec. 18, 2003

(51) Int. Cl.
*A61B 5/06* (2006.01)
(52) U.S. Cl. ............................. 607/91; 607/88; 607/90
(58) Field of Classification Search ............. 607/88–9
See application file for complete search history.

(56) References Cited

U.S. PATENT DOCUMENTS

| | | | |
|---|---|---|---|
| 3,971,643 A * | 7/1976 | Hufton | 55/372 |
| 4,683,888 A * | 8/1987 | Kramer et al. | 607/91 |
| 4,989,600 A | 2/1991 | Collier | |
| 5,058,227 A | 10/1991 | Schoenfelder | |
| 5,335,381 A | 8/1994 | Chang | |
| 5,730,120 A | 3/1998 | Yonkers, Jr. | |
| 5,944,860 A * | 8/1999 | Mack et al. | 55/492 |
| 6,139,568 A | 10/2000 | Doty | |
| 6,363,551 B1 | 4/2002 | Flores | |
| 6,494,901 B1 | 12/2002 | Doty | |
| 6,553,935 B1 | 4/2003 | Penner | |
| 6,802,854 B1 * | 10/2004 | McFarland | 607/91 |

* cited by examiner

*Primary Examiner* — Ahmed Farah
(74) *Attorney, Agent, or Firm* — John D. Gugliotta, PE, Esq

(57) ABSTRACT

A tanning bed air filter is provided that filters incoming air that is provided to tanning beds. An air filter, complete with holder, filter media, and cover screen is provided on the outside of the bed. The filter provides for the filtering of incoming air to the bed, which may be sucked in by internal fans, or by natural convection due to the heating property of the bed. The cover of the invention allows for easy removal, thus exposing the filter media, which may be cleaned or replaced.

7 Claims, 5 Drawing Sheets

TANNING BED WITH AN AIR FILTER

RELATED APPLICATIONS

The present invention was first described in Disclosure Document Number 513,497 filed on May 15, 2003 under 35 U.S.C. §122 and 37 C.F.R. §1.14. There are no previously filed, nor currently any co-pending applications, anywhere in the world.

BACKGROUND OF THE INVENTION

1. Field of the Invention

The present invention relates generally to filter devices and, more particularly, to a universal tanning bed filtration device adapted for mounting to upper and lower tanning units of conventional tanning beds.

2. Description of the Related Art

The perfect, golden tan is a pursuit of many. While many people obtain their tan from sunbathing outside, most of us are not blessed with such a climate that affords this luxury. As such, many of us turn to tanning beds. As with any mechanical device, especially one that draws room air in to help cool its components, a tanning bed is prone to becoming dirty and dusty inside. This dirt and dust not only degrades components, but can also reduce the amount of light emitted from the bed. This is especially a problem in beds that are used almost continually such as those in tanning centers or spas. Accordingly, there exists a need for a means by which dusty and dirty air can be kept from accumulating on internal surfaces and components of tanning beds.

A search of the prior art did not disclose any patents that read directly on the claims of the instant invention; however, the following references were considered related:

U.S. Pat. No. 4,989,600, disclosing a tanning pod.
U.S. Pat. No. 6,553,935, disclosing a pet air bed.
U.S. Pat. No. 5,730,120, disclosing a bed ventilator system.
U.S. Pat. No. 6,363,551, disclosing an air-flow containment and distribution assembly.
U.S. Pat. No. 5,058,227, disclosing an under-bed humidifier.
U.S. Pat. No. 5,335,381, disclosing a bed having a warming device.
U.S. Pat. No. 6,494,901, disclosing a tanning bed.
And, U.S. Pat. No. 6,139,568, disclosing a tanning bed.

Consequently, a need has been felt for providing an apparatus and method specifically adapted for filtration of air through an otherwise conventional tanning bed.

SUMMARY OF THE INVENTION

It is therefore an object of the present invention to provide a tanning bed air filter.

It is a feature of the present invention to provide a universal tanning bed filtration device adapted for mounting to upper and lower tanning units of conventional tanning beds.

Briefly described according to one embodiment of the present invention, a tanning bed air filter is provided that filters incoming air that is provided to tanning beds. An air filter, complete with holder, filter media, and cover screen is provided on the outside of the bed. The filter provides for the filtering of incoming air to the bed, which may be sucked in by internal fans, or by natural convection due to the heating property of the bed. The cover of the invention allows for easy removal, thus exposing the filter media, which may be cleaned or replaced.

The use of the tanning bed air filter provides owners or operators of tanning beds a means of keeping the internals of their beds cleaner while prolonging their maintenance intervals and reducing repairs in a manner, which is quick easy and effective.

An advantage of the present invention is that it protects Internal space of tanning beds from airborne environmental dangers.

Further, a preferred embodiment of the present invention reduces or eliminates damage from dust protects expensive equipment.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

Figure 1A:
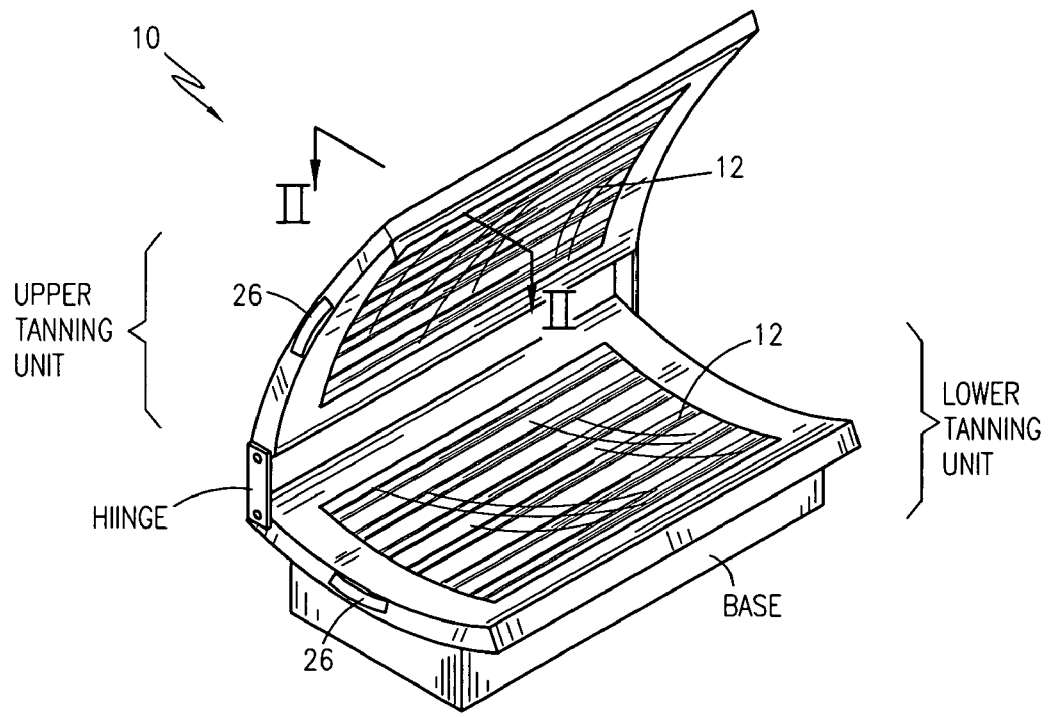
FIG. 1A is a perspective view of a tanning bed according to the PRIOR ART shown in an open position.
Figure 1B:
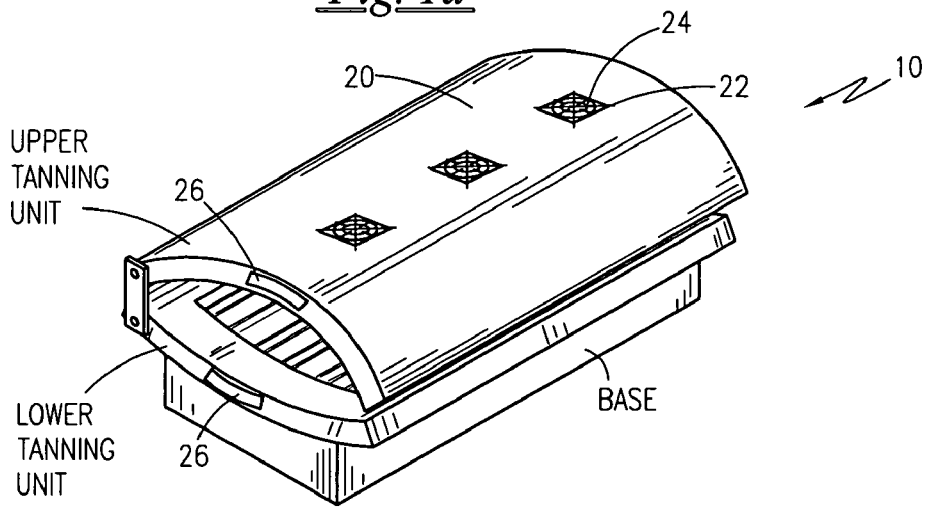
FIG. 1B is a perspective view of a tanning bed according to the PRIOR ART shown in a closed position.

In order to describe the complete relationship of the invention, it is essential that some description be given to the manner and practice of functional utility and description of a typical tanning bed 10 shown in FIG. 1a-1b which has an upper tanning unit and a lower tanning unit connected by hinges so that the upper unit can be opened and a closed in a manner analogous to a clamshell. Both the upper tanning unit and the lower tanning unit each has an outer wall, an inner wall, a pair of oppositely disposed ends, a first longitudinally extending edge, and a second longitudinally extending edge, with the outer wall mounted directly to a base. The upper tanning unit is connected to the base by hinge arms using any conventional fastening device. The hinge arms are part of the hinge mechanism, which can be any device that permits the upper tanning unit to pivot about the base. While typical of a two-unit design, it is also anticipated that tanning beds of only a single, upper tanning unit design do exist and can be configured to benefit from the teachings of the present invention.

In the open position, a person can enter the apparatus to lie down on the lower tanning unit. In the closed position the units form an internal tanning chamber where the person to be tanned is partially surrounded by tanning lamps.

Figure 2:
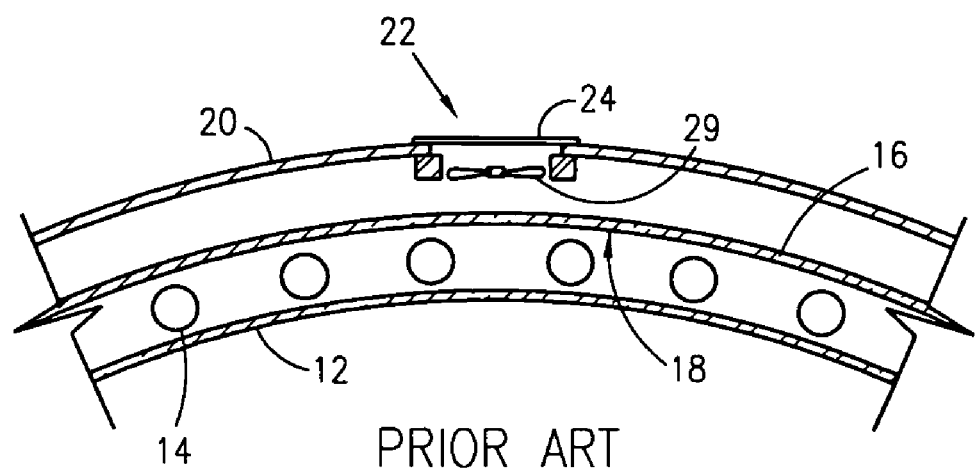
FIG. 2 is a cross sectional view of a tanning bed housing according to the PRIOR ART taken along line II-II of FIG. 1A.

As shown in greater detail in conjunction with FIG. 2, in which a cross section of an upper tanning unit is depicted, but which is analogous to the lower tanning unit, each unit has a clear acrylic plate 12 forming the innermost surface, and rear of the plate 12 is aligned by a plurality of rowed lamps 14. The lamps 14 are between the clear acrylic plate 12 and an aluminum reflector plate 16. The inside of the reflector plate 16 has a polished reflective surface 18, such that radiation emitted from the lamps 14 are reflected toward the clear acrylic plate 12 that facing parts of the person lying with the tanning bed 10. The lower unit has a similar construction, only with the clear acrylic plate 12 upwardly facing. Enclosing the entire tanning mechanism is an outer casing 20 to the tanning unit. The outer casing forms a ventilation orifice 22, and contains a ventilation fan 29 inside the casing 20 to draw cooling air into the unit to cool the aluminum reflector 16, lamps 14 and lamp ballasts (not shown) during operation. A finger guard 24 is then bolted over the orifice 22 to prevent incidental contact with the moving fan 24. An exhaust port 26 is formed at one end to allow for flow and discharge of the air drawn in by the ventilation fan 29.

During normal operation, the ventilation fan 29 of a conventional tanning bed 10 will cause static charge to build up within the housing, such that any dust or particulates are deposited onto the aluminum reflector 16, the lamps 14, lamp ballasts (not shown) or the inside surface of the clear acrylic plate 12. Such deposits are an aesthetic annoyance, but also cloud the transmission of UV radiation, thereby diminishing the effectiveness of the intended use of the device. Currently, the only method of rectifying these problems is to disassembly the unit and clean the surfaces manually, resulting in lost machine time, increased labor and increased likelihood of equipment failure.

Figure 3:
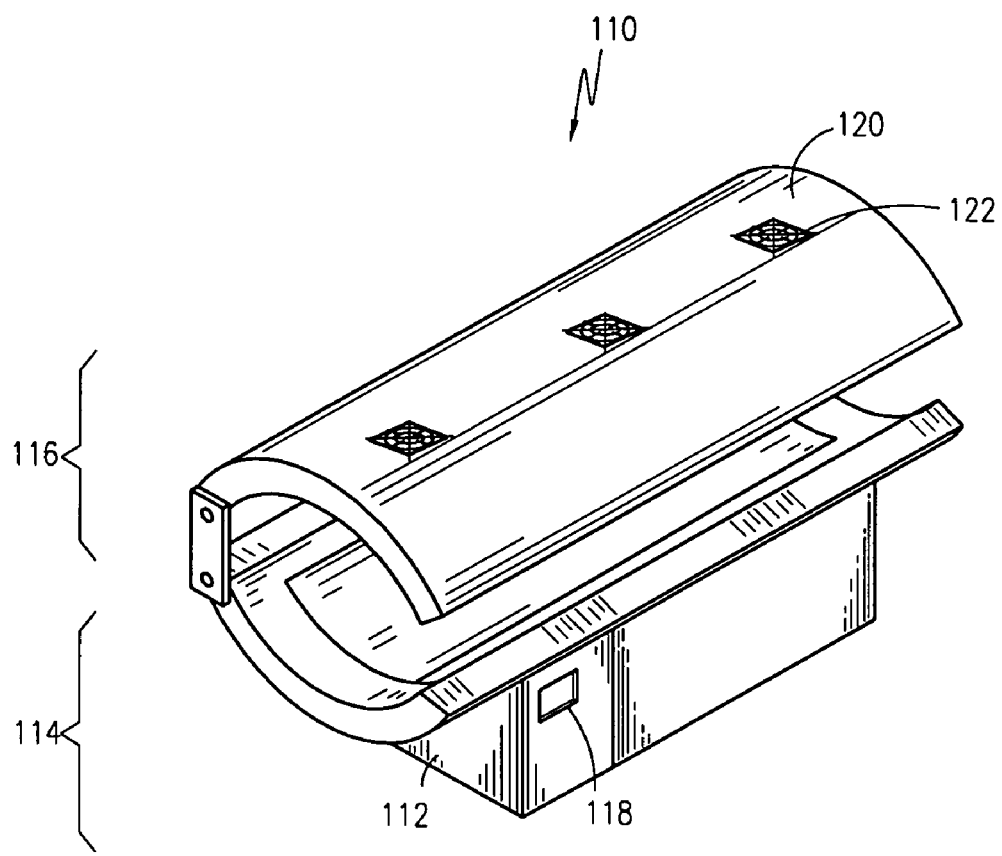
FIG. 3 is a perspective view of a tanning bed incorporating a tanning bed air filter according to the preferred embodiment of the present invention.
Figure 4:
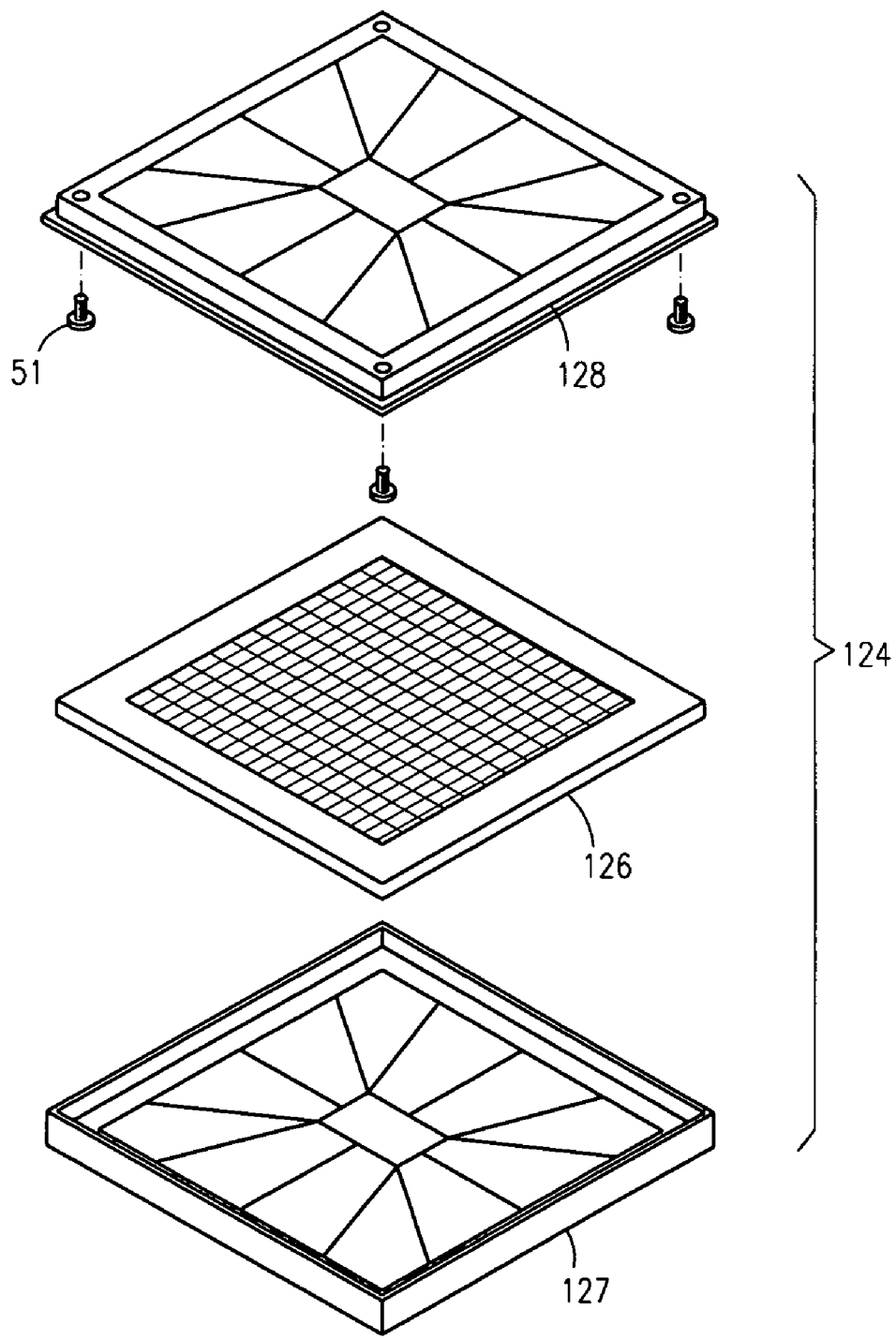
FIG. 4 is an exploded perspective view of a tanning bed air filter according to the preferred embodiment of the present invention.
Figure 5:
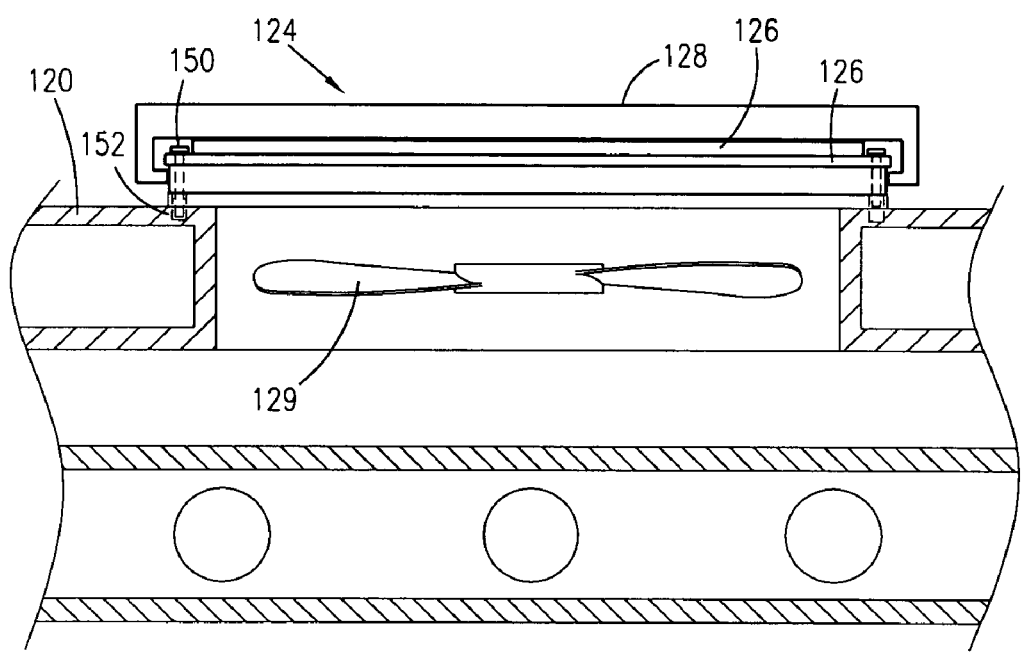
FIG. 5 is a cross sectional view of a tanning bed air filter according to the preferred embodiment of the present invention.

The best mode for carrying out the invention is presented in terms of its preferred embodiment, herein depicted within FIGS. 3-5.

1. Detailed Description of the Figures

Referring now to FIG. 3-5, a view of the preferred embodiment of the tanning bed that is generally referred to by the reference numeral 110. The tanning bed 110 is shown in a closed position and comprises a base 112, a lower tanning unit 114, and an upper tanning unit 116.

The base 112 supports the lower tanning unit 114 and the upper tanning unit 116. The base can have any suitable configuration such as the configuration generally shown in FIG. 3, but is also anticipated as being configured of a single, upper tanning unit without the lower tanning unit. Each tanning unit 114, 116 houses conventional hardware (not shown) that is used to power radiation sources in the upper and lower tanning units 114 and 116. A timer 118 can be affixed to the tanning bed 110, if desired, where it is readily accessible to the user to control the operation of the tanning bed 110.

Although exemplary of the present invention shall be described in reference to its application to the upper tanning bed 116, it is envisioned that the teachings of the present invention can and will also be applied to the lower tanning bed 114 as well. In conjunction with an outer casing 120 forming a ventilation orifice 122, a tanning bed air filter 124 is made to mechanically impinge in such a manner as to attach by frictional impingement in a manner that sandwiches the filter media 126 therebetween. As such and as shown in conjunction with FIG. 4-5, each of a plurality of ventilation fans 129 are supported on and penetrate through the outer wall 120 for providing fluid communication from the outer air to the inner tanning bed space. The otherwise conventional tanning bed ventilation fan 129 further incorporates a filter media 126, such as to filter incoming air that is provided to tanning beds 110. A tanning bed air filter 124, complete with holder 128, filter media 126, and cover screen 127 is provided on the outer casing 120 covering the ventilation orifice 122 on the outer surface of the bed.

In one embodiment, the holder 128 is mechanically attached to the outside of the outer wall 120 to cover each ventilation fan 129, although it is envisioned that the holder 128 may be molded within the outer wall 120 to cover each ventilation fan 129. It is anticipated that this mechanically attachment is by bolts or screws 150 or other conventional means. The filter media 126 provides for the filtering of incoming air to the bed, which may be drawn in by internal fans, or by natural convection due to the heating property of the bed. It is anticipated that many types of filter media can be utilized, including foam, fiberglass, aluminum fiber, or formed paper materials. The cover screen 127 of the invention allows for easy removal, thus exposing the filter media, which may be cleaned or replaced. It is anticipated that the cover screen 127 is made to mechanically impinge with the holder 128 in such a manner as to attach by frictional impingement in a manner that sandwiches the filter media 126 therebetween. In this manner, the cover screen 127 can be easily removed and replaced without hand tools in order to replace or clean the filter media 126, or to change filter media 126 to differing materials in order to change filtering performance.

2. Operation of the Preferred Embodiment

To use the present invention, the standard finger guard is removed from the tanning bed and, using the existing bolt holes 152, the holder 128 is attached. The filter media 126 is selected and placed into the base, and the cover screen 127 is snapped onto the holder 128. Once installed, the apparatus will filter all incoming air of dirt and dust. In some instances fans may have to be reversed in that some installations incorporate ventilation systems that exhaust air outward and draw air into the ends. Such an installation is anticipated as being accommodated within the teachings of the present invention.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. In a tanning bed having an upper tanning unit and a lower tanning unit connected by hinges so that the upper unit can be opened and a closed in a manner analogous to a clamshell, said upper unit having a row of lamps that are intended to tan the upwardly facing parts of the person, and the lower unit having a row of lamps that are intended to tan the downwardly facing parts of said person, said upper tanning unit having an outer wall, an inner wall, and at least one ventilation fan(s) supported on and penetrated through said outer wall and said inner wall for providing fluid communication from said outer air to said inner tanning bed space, wherein the improvement comprises:

a tanning bed air filter affixed over said ventilation fans for filtering incoming air that is provided to said tanning bed;

wherein said tanning bed air filter comprises:
a holder for attachment to said inner wall;
a filter media retained within said holder; and
a cover screen for mechanical attachment to said holder.

2. In the tanning bed of claim 1, wherein said holder is mechanically attached to said inner wall to cover each of said ventilation fans, said mechanical attachment being by threaded fastener of an otherwise conventional means.

3. In the tanning bed of claim 1, wherein said holder is molded within said outer wall to cover each of said ventilation fans.

4. In the tanning bed of claim 1, wherein said filter media is selected from the group comprising foam, fiberglass, aluminum fiber, and paper materials.

5. In the tanning bed of claim 1, wherein said cover screen is made to mechanically impinge with said holder in such a manner as to attach by frictional impingement in a manner that sandwiches said filter media therebetween.

6. A tanning bed filter comprising a universal tanning bed filtration device adapted for mounting to upper tanning units of conventional tanning beds over at least one of the existing ventilation fans for filtering incoming air that is provided to said tanning bed wherein said tanning bed air filter comprises:
    a holder attached to said ventilation fan;
    a filter media retained within said holder; and
    a cover screen for mechanical attachment to said holder, wherein said cover screen is made to mechanically impinge with said holder in such a manner as to attach by frictional impingement in a manner that sandwiches said filter media therebetween.

7. A tanning bed filter comprising a universal tanning bed filtration device adapted for mounting to lower tanning units of conventional tanning beds over at least one of the existing ventilation fans for filtering incoming air that is provided to said tanning bed, wherein said tanning bed air filter comprises:
    a holder mechanically attached to said ventilation fan by threaded fasteners;
    a filter media retained within said holder; and
    a cover screen for mechanical attachment to said holder, wherein said cover screen is made to mechanically impinge with said holder in such a manner as to attach by frictional impingement in a manner that sandwiches said filter media therebetween.

\* \* \* \* \*